United States Patent [19]

Stentz et al.

[11] Patent Number: 5,013,560

[45] Date of Patent: May 7, 1991

[54] MICROBIALLY-STABLE BISMUTH-CONTAINING LIQUID PHARMACEUTICAL SUSPENSIONS

[75] Inventors: Laura L. Stentz, Fairfield; Jerry R. Maney, Mason; Thomas E. Sox, Sharonville, all of Ohio

[73] Assignee: The Procter & Gamble Company, Cincinnati, Ohio

[21] Appl. No.: 324,927

[22] Filed: Mar. 17, 1989

[51] Int. Cl.$^5$ .................. A01N 59/16; A01N 55/02; A61K 33/24; A61K 31/29
[52] U.S. Cl. .................. 424/653; 514/503; 514/867; 514/872
[58] Field of Search .............. 514/503, 867, 872; 424/653

[56] References Cited

U.S. PATENT DOCUMENTS

| | | | |
|---|---|---|---|
| 3,927,205 | 12/1975 | Ohno et al. | 424/80 |
| 4,120,946 | 10/1978 | Queille et al. | 424/4 |
| 4,443,433 | 4/1984 | Knecht et al. | 424/157 |
| 4,482,542 | 11/1984 | Schneider et al. | 424/157 |
| 4,788,180 | 11/1988 | Bloch | 514/26 |

OTHER PUBLICATIONS

Andrew et al., "The Revival of Injured Microbes", *The Society for Applied Bacteriology, Symposium Series No.* 12, pp. 302–303 (1984).
*Antimicrobials in Foods*, Chapter 2 (Chipley, J. R.), pp. 11–35 (1983).
*Antimicrobials in Foods*, Chapter 6 (Sofos et al.), pp. 141–175 (1983).
Beuchat, "Synergistic Effects of Potassium Sorbate and Sodium Benzoate on Thermal Inactivation of Yeasts", *Journal of Food Science*, vol. 46, pp. 771–777 (1981).
Beuchat, "Influence of Potassium Sorbate and Sodium Benzoate on Heat Inactivation of *Aspergillus flavus, Penicillium puberulum* and *Geotrichum candidum*", *Journal of Food Protection*, vol. 44(6), pp. 450–454 (Jun. 1981).
Rushing and Senn, *Proc. Fla. State Hortic. Soc.*, vol. 76, p. 271 (1963).

*Primary Examiner*—Thurman K. Page
*Assistant Examiner*—C. Azpuru
*Attorney, Agent, or Firm*—Kim William Zerby; Douglas C. Mohl; Richard C. Witte

[57] ABSTRACT

Microbially-stable liquid pharmaceutical suspensions for oral administration comprising a bismuth-containing pharmaceutical agent, benzoic acid, sorbic acid, a suspension system and water, and wherein said compositions have a pH within the range of from about 3.0 to about 5.5. These compositions are efficacious, and have good aesthetics and good storage stability.

15 Claims, No Drawings

MICROBIALLY-STABLE BISMUTH-CONTAINING LIQUID PHARMACEUTICAL SUSPENSIONS

BACKGROUND OF THE INVENTION

The present invention relates to microbially-stable liquid pharmaceutical compositions comprising suspended bismuth-containing pharmaceutical agents and a benzoic acid/sorbic acid preservative system. In particular, it relates to efficacious, microbially-stable, highly palatable liquid bismuth-containing pharmaceutical compositions suitable for oral administration.

Liquid suspensions containing bismuth are well known (e.g., De-Nol sold by Gist-Brocades, N.V.; Pepto-Bismol ® sold by The Procter & Gamble Company). Such compositions are used widely for a variety of gastrointestinal disorders such as diarrhea and nausea and, more recently, have been used for treating *C. pylori* infections of the gastrointestinal tract. These compositions must be microbially stable, i.e., resistant to growth of bacteria, molds, yeast and fungi, during manufacture and storage. This includes resistance to microbial growth after the consumer has opened the composition's container.

While there are seemingly an unending number of preservative agents known in the literature, one must be concerned about a myriad of factors when deciding on the particular preservative to be used in a composition. Just a few of these considerations are: impact on taste and flavor system, compatibility with the suspension system and color and pharmaceutical agent, stability of the preservative in the particular container, effectiveness of the preservative against the microbial growth possible in the compositions, the pH of the composition, etc., all which can adversely affect the aesthetics and/or effectiveness of the pharmaceutical agent and/or preservative system.

This large number of known preservative agents includes benzoates and sorbates. For example, see: *Antimicrobials in Foods* (published by Marcel Dekker, Inc., New York; 1983; Branen and Davidson, Editors) Chapters 2 and 6; *The Revival of Injured Microbes, The Society for Applied Bacteriology Symposium Series No.* 12 (Academic Press, New York; 1984; Andrew and Russell, Editors) pages 302-303; Rushing and Senn, *Proc. Fla. State Hortic. Soc.*, 76, 271 (1963); Beuchat, *J. Food Protection*, 44(6), 450-454 (1981); and Beuchat, *J. Food Science* 46 771-777 (1981); the disclosures of all these publications being incorporated herein by reference in their entirety. Pharmaceutical compositions in which benzoates and sorbates are noted as optional components are described in: U.S. Pat. No. 3,927,205, to Ohno et al., issued Dec. 16, 1975; U.S. Pat. No. 4,120,946, to Queuille et al., issued Oct. 17, 1978; U.S. Pat. No. 4,443,433, to Knecht et al., issued Apr. 17, 1984; and U.S. Pat. No. 4,482,542, to Schneider et al., issued Nov. 13, 1984; the disclosures of all these patents being incorporated herein by reference in their entirety.

In spite of the large amount of research aimed at developing efficacious and microbially-stable liquid bismuth-containing compositions, there is a continuing need to provide such compositions which are efficacious and have good aesthetics and good storage stability. It has been discovered that a preservative system comprising low levels of benzoic acid and low levels of sorbic acid is particularly well suited for use in liquid bismuth-containing suspensions. Such a preservative system has several benefits, including: little or no negative impact on product aesthetics (e.g., taste, color, suspension system), preservative effectiveness especially well suited for the pH range encountered over the life of the composition, compatibility of the preservative system with both glass and plastic containers, better preservative activity than either agent alone at these low concentrations, and/or stabilizing effects on the pH of the composition over its life.

It is therefore an object of the present invention to provide microbially-stable bismuth-containing liquid suspensions which are aesthetically acceptable, have good storage stability, and have good preservative activity An object of the present invention is also to provide liquid bismuth-containing compositions which are resistant to microbial contamination and/or growth. A further object is to provide compositions that are believed to have less propensity to change pH over the shelf life of the composition, and to provide effective preservation of the compositions over that pH range. In addition, it is an object to provide such compositions that are compatible with a variety of containers, including glass and plastic bottles.

These and other objects of the present invention will become readily apparent from the detailed description which follows.

All percentages and ratios used herein are by weight unless otherwise specified, and all measurements are made at 25 C unless otherwise specified.

SUMMARY OF THE INVENTION

The present invention relates to microbially-stable liquid pharmaceutical suspensions for oral administration. These compositions comprise: (a) from about 0.1% to about 10% of a bismuth-containing pharmaceutical agent; (b) from about 0.01% to about 0.075% of benzoic acid; (c) from about 0.01% to about 0.04% of sorbic acid; (d) from about 0.1% to about 10% of a suspension system; and (e) from about 80% to about 99% water, and wherein further said liquid composition has a pH within the range of from about 3.0 to about 5.5.

DETAILED DESCRIPTION OF THE INVENTION

The present compositions comprise the following components: (a) bismuth-containing pharmaceutical agent; (b) benzoic acid; (c) sorbic acid; (d) a suspension system; and (e) water. The pH of the compositions of the present invention is within the range of from about 3.0 to about 5.5, and preferably within from about 3.0 to about 4.2. The essential and optional components for use in the compositions of the present invention, and the amounts to be utilized, are described in detail hereinafter.

The term "pharmaceutically-acceptable", as used herein, means that the components present in the compositions of the present invention are compatible and suitable for oral administration to a human or lower animal. The term "compatible", as used herein, means that the components of the pharmaceutical compositions are capable of being commingled with each other in a manner such that there is no interaction which would substantially reduce the pharmaceutical efficacy of the pharmaceutical compositions, or the effectiveness of the preservatives, under ordinary use situations. Pharmaceutically-acceptable components for use herein must, of course, be of sufficiently high purity and sufficiently low toxicity to render them suitable for oral administration to the human or lower animal being treated.

(a) Bismuth-Containing Pharmaceutical Agents:

The pharmaceutical compositions of the present invention comprise a bismuth-containing pharmaceutical agent, preferably in the form of a pharmaceutically-acceptable salt. Such bismuth-containing pharmaceutical agents include, for example, bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. More preferred are bismuth subcitrate, bismuth subsalicylate, and mixtures thereof.

These agents are well known in the art, and are commercially available. Their formulation and use in commercial compositions are also well known, being sold, for example, as De-Nol (bismuth subcitrate; sold by Gist-Brocades, N.V.), and Pepto-Bismol ® (containing bismuth subsalicylate; sold by The Procter & Gamble Company).

The microbially-stable liquid pharmaceutical compositions of the present invention typically comprise, by weight, from about 0.1% to about 10% of a bismuth-containing pharmaceutical agent, preferably from about 0.5% to about 5%, and more preferably from about 1% to about 4%.

(b) Benzoic Acid:

This essential component comprises from about 0.01% to about 0.075%, preferably from about 0.01% to about 0.06%, and more preferably from about 0 025% to about 0.05%, of the liquid compositions of the present invention. It is to be recognized that while benzoic acid is very preferably added in its acid form during the preparation of the compositions herein, pharmaceutically-acceptable salts of benzoic acid may be used and then the pH adjusted to within the desired range. Furthermore, it is to be recognized that within the pH range of the compositions herein, the benzoic acid will be in equilibrium with its unprotonated species, with said equilibrium being pH dependent. The weight percent ranges of this component as described hereinabove are by weight of the protonated species, whether or not all of the benzoic acid is in the protonated form in the composition.

(c) Sorbic Acid

This essential component comprises from about 0.01% to about 0.04%, preferably from about 0.01% to about 0.03%, and more preferably from about 0.0125% to about 0.025%, of the liquid compositions of the present invention. As noted hereinbefore for benzoic acid, it is to be recognized that while sorbic acid is very preferably added in its acid form during the preparation of the compositions herein, pharmaceutically-acceptable salts of sorbic acid may be used and the pH adjusted to within the desired range. Furthermore, it is to be recognized that within the pH range of the compositions herein, the sorbic acid will be in equilibrium with its unprotonated species, with said equilibrium being pH dependent. The weight percent ranges of this component as described hereinabove are by weight of the protonated species, whether or not all of the sorbic acid is in the protonated form in the composition.

(d) Suspension System

The compositions herein also comprise a suspension system capable of suspending the bismuth-containing pharmaceutical agent and the other essential and optional components in an aqueous media. Preferred suspension systems for use herein comprise a pharmaceutically-acceptable non-ionic cellulose ether polymer, magnesium aluminum silicate, and, most preferably, mixtures thereof.

Preferred non-ionic cellulose ether polymers are selected from the group consisting of alkylcelluloses (e.g., methylcellulose), hydroxyalkylalkylcelluloses (e.g., hydroxypropylmethylcellulose: hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Most preferred are alkylcelluloses, especially methylcellulose. Pharmaceutically-acceptable non-ionic cellulose ether polymers are well known in the art, and are described in more detail in "Handbook of Water-Soluble Gums and Resins" (McGraw-Hill Book Company, New York; 1980; Davidson, editor), Chapters 3, 12, and 13, the disclosures of which are incorporated herein by reference in their entirety.

Representative examples of pharmaceutically-acceptable non-ionic cellulose ether polymers useful in the compositions of the present invention are: Methocel A ® (methylcellulose, sold by The Dow Chemical Company); Metolose SM ® (methylcellulose, sold by Shin Etsu Chemical Products, Ltd.); and Methocel E ® (hydroxypropylmethylcellulose, sold by The Dow Chemical Company).

The pharmaceutical compositions of the present invention typically comprise, by weight, from about 0.1% to about 5% as a non-ionic cellulose ethyl polymer, preferably from about 0.1% to about 3%, and more preferably from about 0.5% to about 1.5%.

It is further preferred that the suspension system of the compositions of the present invention comprise a magnesium aluminum silicate. Magnesium aluminum silicate (or aluminum magnesium silicate) is of the formula $Al_2MgO_8Si_2$, occurring naturally in such smectite minerals as colerainite, saponite, and sapphirine. Refined magnesium aluminum silicates useful herein are readily available, such as Veegum, magnesium aluminum silicate manufactured by R. T. Vanderbilt Company, Inc.

The pharmaceutical compositions of the present invention typically comprise, by weight, from about 0.1% to about 5% of a magnesium aluminum silicate, preferably from about 0.1% to about 3%, and more preferably from about 0.5% to about 1.5%.

Another potentially useful material for suspension systems in the present compositions is xanthan gum, and preferably a mixture of xanthan gum and magnesium aluminum silicate. Xanthan gum is a high molecular weight polysaccharide produced through pure culture fermentation of carbohydrates by the microorganism *Xanthomonas camoestris*. Xanthan gum is further described in "Handbook of Water-Soluble Gums and Resins" (McGraw-Hill Book Company, New York; 1980; Davidson, editor) Chapter 24, incorporated by reference herein in its entirety. Xanthan gum is available from a variety of commercial sources, including Rhodigel (sold by Rhone Poulenc Industries) and Keltrol (sold by Kelco Division of Merck & Co., Inc.). Xanthan gum is typically used at a level of from about 0.1% to about 5%, preferably from about 0.1% to about 3%, and more preferably from about 0.5% to about 1.5%.

The suspension systems for the compositions of the present invention typically comprise from about 0.1% to about 10%, preferably from about 0.5% to about 5%, and more preferably from about 1% to about 3%, by weight of the composition.

(e) Water

The liquid compositions of the present invention further comprise from about 80% to about 99%, preferably from about 90% to about 99%, and more preferably from about 93% to about 98% of water.

(f) Optional Components

In addition to the components described hereinbefore, the pharmaceutical compositions of the present invention may comprise additional optional components selected as appropriate for the particular composition being prepared. The choice of pharmaceutically-acceptable optional components to be used in the compositions of the present invention is basically determined by the properties, especially aesthetic properties, desired for the composition. Pharmaceutically-acceptable optional components suitable for the preparation of compositions herein for oral administration are well known in the art.

Some examples of substances which can serve as pharmaceutically-acceptable optional components are sugars such as lactose, glucose and sucrose; non-nutritive sweeteners such as saccharin, aspartame, acesulfame, and cyclamate; coloring agents; flavoring agents such as methyl salicylate; etc. A preferred optional component is salicylic acid which may be used to reduce pH and/or provide some preservative benefit. Other compatible pharmaceutical additives and actives (e.g., NSAI drugs; $H_2$ receptor blocking anti-secretory agents) may be included in the pharmaceutically-acceptable optional components for use in the compositions of the present invention.

The following example further describes and demonstrates an embodiment within the scope of the present invention. This example is given solely for the purpose of illustration, and is not to be construed as a limitation of the present invention since many variations thereof are possible without departing from its spirit and scope.

EXAMPLE I

A composition of the present invention is prepared using conventional methods and having the following components.

| Components | Weight % |
| --- | --- |
| Veegum[1] | 0.986 |
| Methylcellulose[2] | 1.08 |
| Bismuth subsalicylate | 3.50 |
| FD & C red #3 | 0.0364 |
| FD & C red #40 | 0.00539 |
| Sodium saccharin | 0.0608 |
| Sodium salicylate | 0.0598 |
| Salicylic acid | 0.0705 |
| Methyl salicylate | 0.088 |
| Peppermint oil | 0.0074 |
| Benzoic Acid | 0.050 |
| Sorbic Acid | 0.025 |
| Purified water | Q.S. |

[1]Magnesium aluminum silicate manufactured by R. T. Vanderbilt Company, Inc.
[2]Methocel A ®, supplied by The Dow Chemical Company.

This composition may be prepared by first mixing the Veegum in chilled water, and then adding to this mixture a warm aqueous slurry of methylcellulose followed by FD&C Red No. 3, bismuth subsalicylate slurry, FD&C Red No. 40, sodium saccharin, sodium salicylate, peppermint oil, and a slurry of salicylic acid, benzoic acid, sorbic acid, and methyl salicylate. Finally, sufficient water is added to dilute the composition to the desired final weight, and the composition is mixed to homogeneity. The pH of this composition immediately following preparation is about 3.5.

Ingestion of two tablespoons (approximately 30 milliliters containing about 1,050 milligrams of bismuth subsalicylate) of this liquid four times per day is effective for treating diarrhea, heartburn, and nausea. Similarly, a microbially-stable and effective composition may be prepared and orally administered by using bismuth subcitrate in place of the bismuth subsalicylate in the above formulation at the same bismuth level.

What is claimed is:

1. Microbially-stable liquid pharmaceutical suspensions for oral administration comprising:
    (a) from about 0.1% to about 10% of a bismuth-containing pharmaceutical agent;
    (b) from about 0.01% to about 0.075% of benzoic acid;
    (c) from about 0.01% to about 0.04% of sorbic acid;
    (d) from about 0.1% to about 10% of a suspension system; and
    (e) from about 80% to about 99% water, and wherein further said liquid composition has a pH within the range of from about 3.0 to about 5.5.

2. Microbially-stable liquid pharmaceutical suspensions according to claim 1 wherein said bismuth-containing agent is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof.

3. Microbially-stable liquid pharmaceutical suspensions according to claim 1 wherein said suspension system comprises a pharmaceutically-acceptable non-ionic cellulose ether polymer, magnesium aluminum silicate, xanthan gum, or mixtures thereof.

4. Microbially-stable liquid pharmaceutical suspensions according to claim 2 wherein said bismuth-containing pharmaceutical agent is selected from the group consisting of bismuth citrate, bismuth subcitrate, tripotassium dicitrato bismuthate, bismuth tartrate, bismuth subsalicylate, and mixtures thereof.

5. Microbially-stable liquid pharmaceutical compositions according to claim 4 wherein said suspension system is selected from the group consisting of methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, xanthan gum, magnesium aluminum silicate, and mixtures thereof.

6. Microbially-stable liquid pharmaceutical suspensions according to claim 2 wherein said suspension system comprises xanthan gum and magnesium aluminum silicate.

7. Microbially-stable liquid pharmaceutical suspensions according to claim 2 wherein said suspension system comprises methylcellulose and magnesium aluminum silicate.

8. Microbially-stable liquid pharmaceutical suspensions for oral administration comprising:
    (a) from about 0.5% to about 5% of a bismuth-containing pharmaceutical agent selected from the group consisting of bismuth subcitrate, bismuth subsalicylate, and mixtures thereof;

(b) from about 0.01% to about 0.06% of benzoic acid;
(c) from about 0.01% to about 0.03% of sorbic acid;
(d) from about 0.5% to about 5% of a suspension system selected from the group consisting of nonionic cellulose ether polymer, magnesium aluminum silicate, and mixtures thereof; and
(e) from about 90% to about 99% water, and wherein further said liquid composition has a pH within the range of from about 3.0 to about 4.2.

9. Microbially-stable liquid pharmaceutical suspensions according to claim 8 wherein said bismuth-containing pharmaceutical agent is bismuth subcitrate.

10. Microbially-stable liquid pharmaceutical suspensions according to claim 8 wherein said bismuth-containing pharmaceutical agent is bismuth subsalicylate.

11. Microbially-stable liquid pharmaceutical suspensions according to claim 9 wherein said suspension system comprises methylcellulose and magnesium aluminum silicate.

12. Microbially-stable liquid pharmaceutical suspensions according to claim 10 wherein said suspension system comprises methylcellulose and magnesium aluminum silicate.

13. Microbially-stable liquid pharmaceutical suspensions for oral administration comprising:
(a) from about 1% to about 4% of a bismuth-containing pharmaceutical agent selected from the group consisting of bismuth subcitrate, bismuth subsalicylate, and mixtures thereof;
(b) from about 0.025% to about 0.05% of benzoic acid;
(c) from about 0.0125% to about 0.025% of sorbic acid;
(d) from about 1% to about 3% of a suspension system, wherein said suspension system comprises methylcellulose and magnesium aluminum silicate; and
(e) from about 93% to about 98% water, and wherein further said liquid composition has a pH within the range of from about 3.0 to about 4.2.

14. Microbially-stable liquid pharmaceutical suspension according to claim 13 wherein said bismuth-containing pharmaceutical agent is bismuth subcitrate.

15. Microbially-stable liquid pharmaceutical suspension according to claim 13 wherein said bismuth-containing pharmaceutical agent is bismuth subsalicylate.

* * * * *